US008323968B2

(12) United States Patent (10) Patent No.: US 8,323,968 B2
O'Brien et al. (45) Date of Patent: Dec. 4, 2012

(54) OSTEOPONTIN FOR THE PREDICTION AND TREATMENT OF CARDIOVASCULAR DISEASES

(75) Inventors: Timothy O'Brien, Galway (IE); Frank Barry, Oughterard (IE); Aaron Yie Loong Liew, Galway (IE); Afshin Samali, Galway (IE); Angela Duffy, Rahoon (IE)

(73) Assignee: National University of Ireland, Galway, Galway (IE)

( * ) Notice: Subject to any disclaimer, the term of this patent is extended or adjusted under 35 U.S.C. 154(b) by 0 days.

(21) Appl. No.: 12/528,610

(22) PCT Filed: Mar. 3, 2008

(86) PCT No.: PCT/EP2008/052578
§ 371 (c)(1),
(2), (4) Date: Dec. 23, 2009

(87) PCT Pub. No.: WO2008/107422
PCT Pub. Date: Sep. 12, 2008

(65) Prior Publication Data
US 2010/0150877 A1 Jun. 17, 2010

(30) Foreign Application Priority Data

Mar. 2, 2007 (IE) ..................................... 2007/0136
Dec. 10, 2007 (IE) ..................................... 2007/0901

(51) Int. Cl.
*C12N 15/63* (2006.01)
*C12N 5/00* (2006.01)
*C12N 5/08* (2006.01)
*C07K 1/00* (2006.01)

(52) U.S. Cl. ......... 435/372; 435/325; 435/455; 530/350
(58) Field of Classification Search .................. 435/325, 435/372, 455; 530/350
See application file for complete search history.

(56) References Cited

U.S. PATENT DOCUMENTS 6,414,219 B1 7/2002 Denhardt
2003/0158113 A1* 8/2003 Giachelli et al.

FOREIGN PATENT DOCUMENTS

| JP | 2004-222836 | 8/2004 |
| WO | 03/046135 | 6/2003 |
| WO | 2006/060779 | 6/2006 |
| WO | 2006/130690 | 12/2006 |
| WO | 2007/012764 | 2/2007 |
| WO | 2007/024649 | 3/2007 |

OTHER PUBLICATIONS

Kramer et al., 2004, J Dent Res, vol. 83, No. 1, p. 27-34.*
Hwang et al., 1994, The Journal of Biological Chemistry, vol. 269, No. 1, pp. 711-715.*
Catelas et al., 2006, Tissue Engineering, vol. 12, No. 8, p. 2385-2399.*
Nuttelman et al., 2006, J. Biomed Mater Res, vol. 76A, p. 183-195.*
Ingram, et al., "Identification of a novel hierarchy of endothelial progenitor cells using human peripheral and umbilical cord blood," Blood. 2004, vol. 104, No. 9; pp. 2752-2760.
Denhardt, et al., "Osteopontin-Induced modifications of Cellular Functions," Annals New York Academy of Sciences. 1995, vol. 760, pp. 127-142.
Lin, et al. "Origins of Circulating Endothelial Cells and Endothelial Outgrowth from Blood," J Clin Invest. 2000, vol. 105; pp. 71-77.
Ballard, et al., "Vascular tenascin-C regulates cardiac endothelial Phenotype and neovascularization," The FASEB Journal. Feb. 6, 2006, vol. 20, pp. 717-719, Online express article 10.1096/fj.05-5131fje; pp. 1-22.
Rivard, et al., "Rescue of Diabetes-Related Impairment of Angiogenesis by Intramuscular Gene Therapy with Adeno-VEGF," American Journal of Pathology. Feb. 2, 1999, vol. 154, No. 2; pp. 355-363.
Muramatsu, et al., "Inhibition of osteopontin expression and function in oral cancer cell lines by antisense oligonucleotides," Cancer Letters. 2005, vol. 217; pp. 87-95.
Wai, et al., "Osteopontin silencing by small interfering RNA suppresses in vitro and in vivo CT26 murine colon adenocarcinoma metastasis," Carcinogenesis. 2005, vol. 26, No. 4; pp. 741-751.
Ito, et al., "An Inducible Short-Hairpin RNA Vector against Osteopontin Reduces Metastatic Potential of Human Esophageal Squamous Cell Carcinoma in vitro and in vivo," Clin Cancer Res. Feb. 15, 2006, vol. 12, No. 4; pp. 1308-1316.
Hu, et al., "Overexpression of Osteopontin Is Associated with More Aggressive Phenotypes in Human Non-Small Cell Lung Cancer," Clin Cancer Res. Jul. 1, 2005, vol. 11, No. 13; pp. 4646-4652.
Zhou, et al., "Osteopontin Expression Correlates with Melanoma Invasion," The Journal of Investigative Dermatology. May 2005, vol. 124, No. 5; pp. 1044-1052.
Hirama, et al., "Osteopontin overproduced by tumor cells acts as a potent angiogenic factor contributing to tumor growth," Cancer Letters. 2003, vol. 198; pp. 107-117.
Haubner, et al., "Noninvasive Visualization of the Activated avb3 Integrin in Cancer Patients by Positron Emission Tomography and [18F]Galacto-RGD," PLoS Medicine. Mar. 2005, vol. 2, No. 3; pp. 244-252.
Loomans, et al., "Endothelial Progenitor Cell Dysfunction in Type 1 Diabetes: Another Consequence of Oxidative Stress?," Antioxidants & Redox Signaling. 2005, vol. 7, Nos. 11-12; pp. 1468-1475.
Fadini, et al., "Endothelial Progenitor Cells and the Diabetic Paradox," Diabetes Care. Mar. 3, 2006, vol. 29, No. 3; pp. 714-716.
Asnaghi, et al., "Increased clonogenic potential of circulating endothelial progenitor cells in patients with type 1 diabetes and proliferative retinopathy," Diabetologia. 2006, vol. 49; pp. 1109-1111.
Eggermann, et al., "Endothelial progenitor cell culture and differentiation in vitro: a methodological comparison using human umbilical cord blood," Cardiovascular Research. 2003, vol. 58; pp. 478-486.
Urbich, et al., "Endothelial Progenitor Cells," TCM. 2004, vol. 14, No. 8; pp. 318-322.

(Continued)

*Primary Examiner* — Shin-Lin Chen
(74) *Attorney, Agent, or Firm* — Michael A. Davitz (57) ABSTRACT

Osteopontin for the prediction and treatment of cardiovascular diseases The present invention relates to the use of endothelial progenitor cells (EPCs) and osteopontin for the treatment of cardiovascular diseases or complications. The invention also relates to the use of EPC osteopontin levels as a marker of the risk of the development of these cardiovascular complications. In particular, the invention provides compositions and methods based on osteopontin and the genes encoding osteopontin.

3 Claims, 7 Drawing Sheets

OTHER PUBLICATIONS

Takahashi, et al., "Transplantation of Endothelial Progenitor Cells into the Lung to Alleviate Pulmonary Hypertension in Dogs," Tissue Engineering. 2004, vol. 10, Nos. 5-6; pp. 771-779.

He, et al., "Transplantation of Circulating Endothelial Progenitor Cells Restores Endothelial Function of Denuded Rabbit Carotid Arteries," Stroke. Oct. 2004; pp. 2378-2384.

Griese, et al., "Isolation and Transplantation of Autologous Circulating Endothelial Cells Into Denuded Vessels and Prosthetic Grafts: Implications for Cell-Based Vascular Therapy," Circulation. Nov. 25, 2003; pp. 2710-2715.

Kubota, et al., "Transplanted Endothelial Progenitor Cells Augment the Survival Areas of Rat Dorsal Flaps," Cell Transplantation. 2003, vol. 12; pp. 647-657.

Kalka, et al., "Transplantation of ex vivo expanded endothelial progenitor cells for therapeutic neovascularization," PNAS. Mar. 28, 2000, vol. 97, No. 7; pp. 3422-3427.

Asahara, et al., "Isolation of Putative Progenitor Endothelial Cells for Angiogenesis," Science. Feb. 14, 1997, vol. 275; pp. 964-967.

Walenta, et al., "In vitro differentiation characteristics of cultured human mononuclear cells-implications for endothelial progenitor cell biology," Biochemical and Biophysical Research Communications. 2005, vol. 333; pp. 476-482.

Marcia, et al., "Bone Mineral Density and Its Change in White Women: Estrogen and Vitamin D Receptor Genotypes and Their Interaction," Journal of Bone & Mineral Research. Apr. 1998, vol. 13, No. 4; pp. 695-705.

Fadini, et al., "Circulating Endothelial Progenitor Cells Are Reduced in Peripheral Vascular Complications of Type 2 Diabetes Mellitus," Journal of the American College of Cardiology. 2005, vol. 45, No. 9; pp. 1449-1457.

Tepper, et al., "Human Endothelial Progenitor Cells From Type II Diabetics Exhibit Impaired Proliferation, Adhesion, and Incorporation Into Vascular Structures," Circulation. Nov. 26, 2002; pp. 2781-2786.

Loomans, et al., "Endothelial Progenitor Cell Dysfunction: A Novel Concept in the Pathogenesis of Vascular Complications of Type 1 Diabetes," Diabetes. Jan. 2004, vol. 53; pp. 195-199.

Bellik, et al., "Morphological and phenotypical characterization of human endothelial progenitor cells in an early stage of differentiation," FEBS Letters. 2005, vol. 579; pp. 2731-2736.

Noiri, et al., "Reduced tolerance to acute renal ischemia in mice with a targeted disruption of the osteopontin gene," Kidney International. 1999, vol. 56; pp. 74-82.

Gattorno, et al., "Synovial expression of osteopontin correlates with angiogenesis in juvenile idiopathic arthritis," Rheumatology. 2004, vol. 43; pp. 1091-1096.

Asou, et al., "Osteopontin Facilitates Angiogenesis, Accumulation of Osteoclasts, and Resorption in Ectopic Bone," Endocrinology. 2001, vol. 142, No. 3; pp. 1325-1332.

Hamada, et al., "Angiogenic activity of osteopontin-derived peptide SVVYGLR," Biochemical and Biophysical Research Communications. 2003, vol. 310; pp. 153-157.

Masaaki, et al., "Accelerated Reendotheilalization in ApoE Knockout Mice is Mediated by Activated Bone Marrow-Derived Endothelial Progenitor Cells," Circulation, 2005, vol. 112, 17, Suppl. S, p. U219. & 78th Annual Scientific Session of the American-Heart-Association; Dallas, TX, USA; Nov. 13-16, 2005.

Takagi, et al., "Role of Vitronectin Receptor-Type Integrins and Osteopontin in Ischemia-Induced Retinal Neovascularization," Jpn J Ophthalmol. 2002, vol. 46; pp. 270-278.

Zhao, et al., "Impairment of Myocardial Angiogenic Response in the Absence of Osteopontin," Microcirculation. 2007, vol. 14; pp. 233-240.

Schernthaner, et al., "Impaired number and function of circulating endothelial progenitor cells in patients with morbid obesity," Circulation. Oct. 31, 2006, vol. 114, 185.

Okamoto, et al., "Osteopontin and cardiovascular system," Mol Cell Biochem. 2007, vol. 300; pp. 1-7.

Schaper, et al., "Arterial stiffness and remodelling," Diabetologia. 2006, vol. 49.

Kim, et al., "The effect of benfotiamine on endothelial function in patients with type 2 diabetes mellitus," Diabetologia. 2006, vol. 49.

Gottlieb, et al., "Reperfusion injury induces apoptosis in rabbit cardiomyocytes," The Journal of Clinical Investigation. 1994, vol. 94, No. 4, pp. 1621-1628.

Gulati, R et al., "Diverse Origin and Function of Cells With Endothelial Phenotype Obtained from Adult Human Blood," Circ. Res. 2003; vol. 93, pp. 1023-1025.

Hur, J et al. "Characterization of two types of endothelial progenitor cells and their different contributions to neovasculogenesis." Arterioscler. Thromb. Vasc. Biol. 2004; vol. 24, pp. 288-293.

Liew A, et al., "Endothelial progenitor cells: diagnostic and therapeutic considerations." Bioessays. 2006, vol. 28, pp. 261-270.

Willing M, et al., "Bone mineral density and its change in white women: estrogen and vitamin D receptor genotypes and their interaction," J Bone Miner Res. 1998, vol. 13, pp. 695-705.

Uede T, et al., "Osteopontin, a coordinator of host defense system: a cytokine or an extracellular adhesive protein?" Microbiol. Immunol. 1997, vol. 41, No. 9, pp. 641-648.

Tsuchida A, et al., "alpha 1-adrenergic agonists precondition rabbit ischemic myocardium independent of adenosine by direct activation of protein kinase C," Circ. Res. 1994, vol. 75, pp. 576-585.

Fliss H, et al., "Apoptosis in Ischemic and Reperfused Rat Myocardium," Circ. Res. 1996, vol. 79, pp. 949-956.

Ellison J A, et al., "Matrix remodeling after stroke: de novo expression of matrix proteins and integrin receptors," Annals of the New York Academy of Sciences. 1999, vol. 890, pp. 204-222.

Schernthaner GH, et al., "Endothelial progenitor cells are reduced but activated in type 1 diabetic patients with longstanding disease and high HbA(1c)" Diabetologia. 2006, vol. 49, Suppl. 1, pp. 726-727.

* cited by examiner

OSTEOPONTIN FOR THE PREDICTION AND TREATMENT OF CARDIOVASCULAR DISEASES

FIELD OF THE INVENTION

The present invention relates to the use of endothelial progenitor cells (EPCs) and osteopontin for the treatment of cardiovascular diseases or complications. The invention also relates to the use of EPC osteopontin levels as a marker of the risk of the development of these cardiovascular complications. In particular, the invention provides compositions and methods based on osteopontin and the genes encoding osteopontin.

BACKGROUND TO THE INVENTION

The discovery of endothelial progenitor cells (EPCs) by Asahara et al in 1997 has provided an insight into the pathogenesis of many vascular disease states such as ischaemia, restenosis and pulmonary hypertension[1-6]. Urbich et al have recently defined EPCs as highly proliferative non-endothelial cells which are capable of transdifferentiating into endothelial cells[7]. EPCs can be isolated from various sources, including bone marrow, peripheral blood and umbilical cord blood[8-10]. There are two phenotypes of EPCs (early versus late EPCs) which both have distinct proliferative and angiogenic potential[8,11]. The ability to adhere to matrix molecules such as fibronectin, incorporate acLDL and bind lectin remains the commonly used definition for EPCs, but, increasingly, further flow cytometry analysis and immunostaining with various markers such as haematopoeitic markers and endothelial markers are utilised to define EPCs[12-15].

Patients with type 1[16] and type 2[17,18] diabetes mellitus have a lower number of EPCs as compared to healthy volunteers. Patients with type 2 diabetes complicated with peripheral vascular disease have even lower number of EPCs compared to those without complications[18]. EPC number in these patients inversely correlates with glycaemic control[16-18]. EPCs isolated from patients with type 2 diabetes had decreased adhesion to activated endothelial cells, and to matrix molecules such as collagen and fibronectin[17]. EPCs derived from patients with both types of diabetes have impaired ability to form tubules in vitro[16,17]. Furthermore, bone marrow mononuclear cells derived from streptozotocin induced diabetic mouse differentiate less efficiently into EPCs in vitro and are less likely to form tubules than those derived from non-diabetic mice[19]. The conditioned media from EPCs isolated from patient with type 1 diabetes has a reduced angiogenic capacity and may contain inhibitors of tubule formation in vitro[16]. The phenotype of EPCs derived from patients with type 1 diabetes also remains unchanged even after culture in normoglycaemic conditions[16].

Osteopontin (OPN) is an arginine-glycine-aspartic acid (RGD)-containing glycoprotein. It is involved in cell migration, cell survival, regulation of immune cell function, inhibition of calcification and control of tumor cell phenotype[23-25]. Osteopontin enhances tumour growth[26], and its progression[27]. In the setting of primary non-small cell lung cancer, overexpression of OPN increases the aggressiveness of the tumour[28]. Inhibition of OPN expression by either an inducible short-hairpin RNA vector[29], RNA interference[30] or antisense oligonucleotides[31] attenuates the aggressiveness of various tumours.

The prevalence and fatality of cardiovascular disease (CVD) worldwide is testament to the inefficiency of current therapeutic regimes. A fundamental element in many cardiovascular diseases is the loss of functional cardiomyocytes. Apoptosis is associated with many cardiovascular conditions, such as myocardial infarction and heart failure, however the precise mechanisms are unknown. We have identified OPN as a therapeutic target in the prevention of cardiomyocyte death and CVD. Management of expression of candidate genes in patients with cardiovascular disease may greatly enhance their life expectancy. More importantly, regulation of expression of these genes in individuals predisposed to CVD may prevent the onset of the disease. In myocardial complications apoptosis has been observed repeatedly in compromised human hearts and has been proven to be a major contributor to cardiomyocyte death during ischemic/reperfusion (VR) injury and cardiomyopathy (Gottlieb R A, The Journal of Clinical Investigation 1994, Fliss H, Circulation Research 1996).

OBJECT OF THE INVENTION

The object of this invention is to assess the number and function of EPCs derived from patients with cardiovascular diseases, including poorly controlled T1DM cardiovascular disease and to understand the mechanisms underlying cardiovascular diseases. A further objective is to provide compositions and methods for use in the prevention and treatment of cardiovascular diseases including T1DM cardiovascular disease, and resultant symptoms such as diabetic ulcers.

SUMMARY OF THE INVENTION

According to the present invention there is provided a pharmaceutical composition comprising osteopontin together with a pharmaceutically acceptable carrier or excipient. Such a composition finds use in the treatment of vascular diseases, diabetes-associated vascular disease or complications including cardiovascular diseases arising from such diseases. One example of such a complication is foot ulcers, although there are many others.

As used herein the term 'cardiovascular diseases or complications' includes cardiovascular diseases and diabetes associated vascular complications including conditions such as myocardial infarction, ischemia, peripheral vascular disease, ischemia, cerebrovascular disease, coronary vascular diseases and heart failure and it's underlying causes. Such diseases may be due to the presence of risk factors for these vascular diseases such as diabetes mellitus, dyslipidaemia and hypertension.

In a further aspect, the invention provides a composition for the treatment of cardiovascular complications comprising endothelial progenitor cells (EPCs) or mesenchymal stem cells (MSCs) which have been modified to augment osteopontin gene expression together with a pharmaceutically acceptable carrier or excipient. The cardiovascular disease may be associated with diabetes. Overexpression of osteopontin by EPCs or MSCs can be achieved in a variety of ways known to the person skilled in the art, for example by transfecting the cell with liposome or adenovirus encoding OPN gene. Alternatively, EPCs or MSCs can also be preincubated with recombinant OPN prior to transplantation to provide an activated EPC or MSC. In this context activated stem cells are those that have been pre-treated with OPN which renders them more able to form tubules. Thus supplementation with OPN of OPN deficient cells improves their function.

In a further embodiment an OPN coated stent together with administration of EPC/MSCs could be used to enhance the angiogenic effect. The invention also provides a pharmaceutical composition comprising the gene encoding osteopontin or a mutant thereof also encoding functional osteopontin, together with a pharmaceutically acceptable carrier or excipient.

In a further aspect, the invention provides a method for determining whether a subject has cardiovascular disease or is at risk of developing cardiovascular disease by measuring the level of osteopontin expression in the patient and comparing the level with that of a healthy control. Likewise, the invention provides a method for determining whether a subject with diabetes has vascular complications, or is at risk of developing diabetes related vascular complications comprising measuring the level of osteopontin expression in the patient and comparing the level with that of a healthy control. The level of osteopontin expression may be measured in any of blood, tissue, EPCs or serum from a patient.

OPN level is increased in hyperglycaemic states. This may be related to the protective role of OPN in this state. Measuring endogenous OPN level in EPCs may be useful since a low OPN level (as shown herein) implies that these subjects are at risk of developing diabetes related vascular complications in the near future even though the complications have not occurred yet, whereas an elevated endogenous OPN level (Loomans' paper) implies the presence of vascular complications. The OPN level is increased in EPCs to enhance therapeutic neovascularisation. However, since the number of EPCs is reduced in patients with vascular complications, the increased endogenous OPN expression in these EPCs may not be sufficient to augment therapeutic neovascularistion. The endogenous OPN may be dysfunctional. Exogenous functional OPN is required to improve EPC function. EPC may serve as a vector for functional OPN transfer to the area of ischaemic injury. The use of additional EPCs overexpressing functional OPN or activated by OPN, may be the solution for non-invasive treatment of T1DM related vascular complications.

The invention also provides methods of treatment of cardiovascular diseases comprising administering to a patient osteopontin, or a polynucleotide encoding osteopontin, endothelial progenitor cells or mesenchymal stem cells which express or overexpress osteopontin or activated EPCs or MSCs. Co-administration of such EPCs or MSC and osteopontin could also be used in these methods. The polynucleotide encoding osteopontin may be incorporated into an endothelial progenitor cell or mesenchymal stem cell and the transformed cell thus produced being usable in a gene therapy technique for the treatment of cardiovascular disease, including diabetes related vascular complications.

In one embodiment patients with peripheral vascular disease (reduced flow due to atherosclerosis in the leg vessels) may be identified and their EPCs may be harvested by blood draw. The gene for OPN may be delivered to the EPCs by non viral or viral means and in turn these modified cells may be delivered to the patient. Delivery to the patient may by through the vasculature using a device or by direct intramuscular delivery. Similarly the heart muscle or the brain could be treated, although the later would involve only intravascular delivery. The EPCs may be modified virally (e.g. via adenovirus, lentivirus or retrovirus) or non virally (e.g. via electroporation or liposome transmission).

In a still further aspect, the invention provides a method for identifying compounds useful in the treatment of cardiovascular diseases, comprising assessing the ability of the compound to increase osteopontin expression in a cell in which osteopontin expression is otherwise down-regulated. The OPN expression can be measured for example by using quantitative real-time PCR or ELISA. Compounds useful in the treatment of cardiovascular disease include compounds useful in the treatment of diabetes related vascular complications The invention also provides an antibody raised against osteopontin, and a medical device coated with an antibody raised against osteopontin, coated with activated stem cells such as EPCs or coated with stem cells such as EPCs which overexpress osteopontin. MSCs could also be used in this way. The medical device may be a stent, a suture, a bandage or dressing or a prosthesis.

In the methods of the invention the use of a recombinant osteopontin protein may be achieved by direct administration of osteopontin using viral or non-viral vectors, and genetically modified cells such as EPCs or MSCs may be manipulated to overexpress osteopontin using viral or non-viral methods.

Overall the inventors have shown that osteopontin deficiency plays a mechanistic role in diabetic EPC dysfunction and have identified a new therapeutic pathway which can be targeted in diabetic vascular disease. Similarly, the inventors have also shown a role for OPN in cardiovascular disease.

DETAILED DESCRIPTION OF THE INVENTION

Methods
Subject Recruitment
Patients with poorly controlled Type 1 Diabetes Mellitus (as defined by $HbA_{1/c}>10\%$), who are on insulin for more than one year, and not on any other medications were recruited from the Diabetes Day Centre, University College Hospital Galway, Ireland. Ethical approval for this study was obtained from the University College Hospital Galway Clinical Research and Ethical Committee. Patients with micro- or macrovascular complications were excluded from the study. Microvascular complications were defined as the presence of microalbuminuria, diabetic retinopathy and neuropathy. Macrovascular complications were defined as the presence of any previous history of acute coronary syndrome, peripheral vascular disease and cerebrovascular disease. After signing consent, peripheral blood samples were collected from patients with type 1 diabetes mellitus and healthy volunteers.

Isolation of EPCs

EPCs were cultured according to previously described techniques. Briefly, mononuclear cells (MNCs) were isolated by Ficollpaque density centrifugation method. After purification with 3 washing steps, $10 \times 10^6$ or $2 \times 10^6$ MNCs were plated on fibronectin coated, 6-well plates or 4-well glass slides, respectively. Cells were cultured in endothelial cell basal medium-2 (Clonetics) supplemented with EGM-2 single aliquots (Clonetics) consisting of 5% FBS, vascular endothelial growth factors (VEGF), fibroblast growth factor-2, epidermal growth factor, insulin-like growth factor-1, and ascorbic acid. EPCs were confirmed by dual staining with DiI-acetylated low-density lipoprotein and FITC-lectin.

Animal Studies

Diabetes was induced in male New Zealand White rabbit using intravenous injection of alloxan (150 mg/kg). Rabbits with plasma glucose of >22 were included for the study. Phlebotomy was performed via the marginal artery under anaesthesia. This study was approved by the National University Ireland, Galway (NUIG) Animal Care and Use Committee.

EPC Adhesion to Matrix Molecules

Fibronectin (100 g/mL) was coated onto 24-well plates for 2 hours at 37° C. Wells were blocked with 1% BSA in PBS for 2 hours and EPCs ($1 \times 10^5$) were added to each well to attach for 1 hour. Adherent cells were stained with 0.1% crystal violet and rinsed with 10% acetic acid to elute the stain from the cells. Attached cells were quantified by analyzing the optical density of the media at a wavelength of 600 nm with a microtiter plate reader.

Adhesion to Mature Endothelial Cells

A monolayer of human umbilical vein endothelial cells (HUVECs) was prepared 48 hours before the assay by plating $2 \times 10^5$ cells (passage 5 to 8) in each well of 4-well glass slides. HUVECs were pretreated for 12 hours with TNF-alpha (BD Biosciences) (1 ng/mL) or media. EPCs were labeled with diI and $1 \times 10^5$ cells were added to each well and incubated for 3 hours at 37° C. Nonattached cells were gently removed with PBS, and adherent EPCs were fixed with 4% paraformaldehyde and counted by a blinded observer.

Matrigel Tubule Assay

Matrigel (Sigma) was thawed and placed in 4-well glass slides at room temperature for 30 minutes to allow solidification. DiI-labeled EPCs ($2 \times 10^4$) were coplated with $4 \times 10^4$ human umbilical vein endothelial cells (HUVECs) and incubated with and without 5 ug/ml OPN (SIGMA) at 37° C. for 12 hours. Tubule formation was defined as a structure exhibiting a length 4 times its width. The number tubules formed was assessed by a blinded counter. To determine if the effect of osteopontin is RGD dependent, different RGD/RAD concentrations were incubated with osteopontin.

RNA Extraction

Total RNA was isolated from day 4 EPCs using RNeasy Mini Kit (Qiagen) as described by the manufacturer. The concentration of isolated total RNA was analyzed using NanoDrop counter. QuantIt DNA High Sensitivity Kit was used to detect presence of any genomic DNA in the total RNA samples.

Microarray Analysis

Microarray analysis were performed using GeneChip Human Genome U133 Plus 2.0 Affymetrix Array. Gene expression profiles were compared between EPCs derived from patients with poorly controlled T1DM and healthy volunteers, with EPCs derived from healthy volunteers as baseline, using MAS5.1 software (Affymetrix). Fold changes were calculated by comparing transcripts between the two groups. K-mean clustering was used to identify the detected (present or absent) and changed (increased or decreased) calls.

Primer Sequences

Primers were designed using PrimerExpress software and ordered from SIGMA Genosys (Table. 1).

Real Time PCR

The expression study was performed using a 96 well plate on an ABI Prism 7000 Sequence Detection System (Applied Biosystems) with One Step QuantiTect SYBR Green PCR Kit (Qiagen). The reactions were performed according to the manufacturer's instructions with minor modifications. The PCR program was initiated using sample volume of 25 µls at 50° C. for 30 mins for reverse transcription step, 95° C. for 15 mins for activation of Taq DNA polymerase and followed by 40 cycles of 15 seconds at 95° C., and 30 seconds at 60° C. The dissociation curves were generated immediately after the real-time PCR using a temperature range between 60° C. and 95° C. Each samples were analyzed in triplicates. All the reactions were further subjected to electrophoresis on 2% agarose gels stained with SyBrGreen dye to confirm the presence of the expected PCR products.

Murine Hind Limb Ischaemic Model

C57BL/6 (WT) and OPN$^-$/OPN$^-$ mice were purchased from Charles River Lab and Jackson Lab respectively. OPN-KO and WT mice aged between 8-10 weeks of age were used. The mice were housed at the Animal Facility in Regenerative Medicine Institute (REMEDI), NCBES, NUIG. All procedures were approved by the Minister of Health and Children under the Cruelty to Animals Act, 1876. Unilateral hind limb ischemia was created in C57BL/6 and OPN$^-$/OPN$^-$ mice as previously described[32]. In brief, an incision was performed in the skin overlying the middle portion of the left hind limb. After ligation of the proximal end of the femoral artery, the distal portion of the saphenous artery was ligated and the artery as well as, all side branches were dissected free and excised. The skin was closed using an absorbable suture. Of note, the animals were anesthetized with ketamine and xylazine and maintained with isoflurane.

Laser Doppler Blood Flow (LDBF) Assessment

The hind-limb blood flow on both hind limbs and feet were measured using a laser Doppler blood flow (LDBF) analyzer (PeriScan PIMII, Perimed Inc) immediately before surgery, and on postoperative days 0, 7, 14, and 28. Blood flow was displayed as changes in the laser frequency using different color pixels. After scanning, stored images were analyzed to quantify blood flow. To avoid data variations caused by ambient light and temperature, hind limb blood flow was expressed as the ratio of left (ischemic) to right (non-ischemic) LDBF.

Flow Cytometric Analysis

All samples were processed within one hour. Live cells were stained with conjugated antibodies to Sca-1, c-kit, and CD31 (BD Biosciences). FACS ARIA Coulter was used to perform the FACS analysis. The frequency of bone marrow cells positive for the above reagents was determined by a two-dimensional side scatter-fluorescence dot plot analysis of the samples stained with the different reagents, after appropriate gating to exclude granulocytes. Initially, Sca-1+ bone marrow cells were gated and then the resulting population was examined for dual expression of c-kit. For further analysis, Sca-1+ cells were studied for the expression of CD31 using a phycoerythrinconjugated anti-mouse CD31 monoclonal antibody (BD Biosciences), reflecting endothelial differentiation of progenitor cells. Data were processed using the Macintosh CELL Quest software program (BD Biosciences). A single trained operator (T.B.), who was blind to the status of the animal, performed all flow cytometric analyses throughout the study.

Statistical Analysis

Results are expressed as mean±SEM. Comparison between groups was performed by ANOVA. Post hoc analysis and pairwise multiple comparisons were performed using the 2-sided t test with Scheffe adjustment. Probability values <0.05 were considered statistically significant. All analyses were performed with SPSS software (SPSS Ver. 14.0 Inc).

A. Langendorff Treatment of Ex-Vivo Hearts

Male Sprague-Dawley rats (225-250 g) were anesthetized, and hearts were rapidly excised and immediately cannulated to a Langendorff perfusion apparatus using a protocol adapted from Tsuchida et al. (*Circulation Research* 1994). Briefly, hearts were perfused with Krebs-Ringer buffer at a constant pressure of 60 mm Hg. All perfused hearts were stabilized for 20 min on the Langandorff apparatus prior to induction of various treatments. Three hearts were used per treatment group (n=3). Perfused hearts were continuously perfused for 1 h 15 min following stabilisation. To mimic ischemia/reperfusion injury non-preconditioned hearts were continuously perfused for 30 min prior to a 30 min exposure to ischemia (stoppage of Kreb's buffer flow) followed by 15 min of reperfusion (resumption of Kreb's buffer flow). Following treatment hearts were immediately removed to Trizol reagent and homogenized (Invitrogen). Following addition of 20% chloroform samples were mixed by inversion and centrifuged at 12,000×g for 15 min at 2-8° C. The RNA was removed and added to an Eppendorf tube containing 0.5 ml isopropanol and vortexed vigorously to precipitate the RNA. After a 10 min incubation at room temperature, the RNA was pelleted by centrifugation at 12,000×g for 10 min and washed in 1 ml of 75% ethanol. RNA was pelleted by centrifugation at 7,500×g for 5 min, the supernatant removed and the pellet allowed to air-dry at room temperature for 10 min. The pellet was subsequently resuspended in 50 µl of DEPC treated water. RNA was quantified by spectroscopy, based on its absorbance at 260 nm (UV absorbance range). Quantitative PCR was carried out with 2 µg RNA and Oligo (dT) 12-18 (Invitrogen) using AMV Reverse Transcriptase (Sigma). Primers to Glyceraldehyde-3-phosphate dehydrogenase (GAPDH), Osteopontinwere designed to published mRNA sequences from the National Centre for Biotechnology Information (NCBI) using Primer Express software (Applied Biosystems, Foster City, Calif.) and sequence specificity was confirmed by performing a BLAST (NCBI) search. Primer sets were synthesized by MWG Biotech (Ebersberg, Germany).

cDNA quantification standards, containing a known number of cDNA copies of each gene, were prepared by purifying PCR products for each gene using the QIAGEN Qiaquick gel extraction kit. These purified products were then quantified by spectroscopy and appropriate dilutions were made.

Amplification reactions were carried out in real-time, with separate reactions set up for each primer set, each containing 12.5 µl of 1× SYBR Green I PCR Master Mix (Applied Biosystems), 12.5 nM of each primer and 2.5 µl template (1 in 50 dilution of cDNA) in a final volume of 25 µl. Amplification reactions were performed in 96-well optical reaction plates on the ABI 7000. A dissociation curve was generated for each primer set at the end of each run and PCR products were run on 2% agarose gels to confirm the size of the product and the specificity of the primers. cDNA copy numbers for all differentially regulated genes were generated from their respective standard curves and normalised to the housekeeping gene GAPDH. A fold increase was calculated relative to the expression levels of the perfused sample. Real-time RT-PCR was carried out for each of the conditions in triplicate and results were then analysed using a one-way ANOVA followed by Scheffe's test using the statistical package SPSS for Windows version 12.0.1 (SPSS Inc., Chicago, Ill., USA).

B. Ischemia in Primary Neonatal Cardiomyocytes:

Primary cultures of neonatal cardiomyocytes were isolated from 1-4 day old Sprague Dawley rats. Briefly, rats were euthanized and hearts excised. After scalpel homogenization, overnight trypsin digestion at 4° C. and a collagenase treatment for 20 min at 37° C., cardiomyocytes were enriched by Percoll gradient centrifugation (Amersham) and plated at a density of $1 \times 10^5$/ml in DMEM/F12 medium supplemented with 10% newborn calf serum, 100 U/ml penicillin, 100 µg/ml streptomycin, 1 mM sodium pyruvate (Gibco-BRL), 5% insulin transferrin selenite (ITS) liquid supplement media, 100 µM 5-Bromo-2-deoxyuridine on culture plates coated with 0.2% gelatin. Cells were cultured at 37° C. and 5% $CO_2$.

To mimic endogenous ischemia, cultures were exposed to hypoxic conditions ($O_2/N_2/CO_2$, 0.5:94.5:5), using a hypoxia gas chamber (Russkin) in the absence of glucose and serum, using glucose-free DMEM (Gibco-BRL) supplemented with 10 mM 2-deoxyglucose, 100 U/ml penicillin, 100 µg/ml streptomycin, 1 mM sodium pyruvate, 5% ITS liquid supplement media.

Cells were lysed in whole cell lysis buffer (20 mM HEPES, pH 7.5, 350 mM NaCl, 1 mM $MgCl_2$, 0.5 mM EDTA, 0.5 mM EGTA, 1% Igepal-630, 0.5 mM dithiothreitol (DTT), 100 µM PMSF and 1 µg/ml pepstatin). Cellular proteins were separated by electrophoresis on 10% SDS-polyacrylamide gels and transferred onto nitrocellulose membranes. After blocking (5% non-fat milk, 0.05% Tween-20 in PBS), blots were incubated with antibodies to ostiopontin and were visualised using horseradish peroxidise-conjugated secondary antibodies (Pierce) were used at a 1:5,000 dilution. Protein bands were detected with SuperSignal Ultra Chemiluminescent Substrate (Pierce) on X-ray film (Agfa).

Results

Subject Recruitment

Four patients with Type 1 Diabetes Mellitus and four age- and gender-matched healthy volunteers were recruited (Table 2).

Assessment of EPC Number

Figure 1:
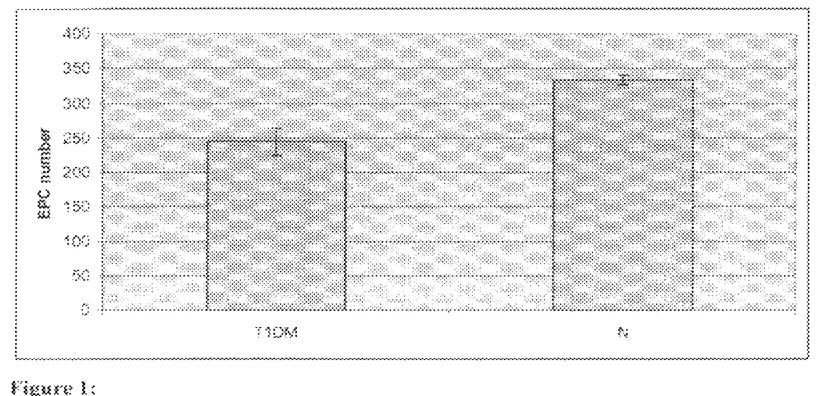
FIG. 1: EPC number in patients with T1DM and healthy volunteers.

Patients with T1DM have lower number of EPCs as compared to healthy volunteers (244+/−20 vs 334+/−7, p=0.02) (FIG. 1).

Adhesion to Matrix Molecules

Figure 2:
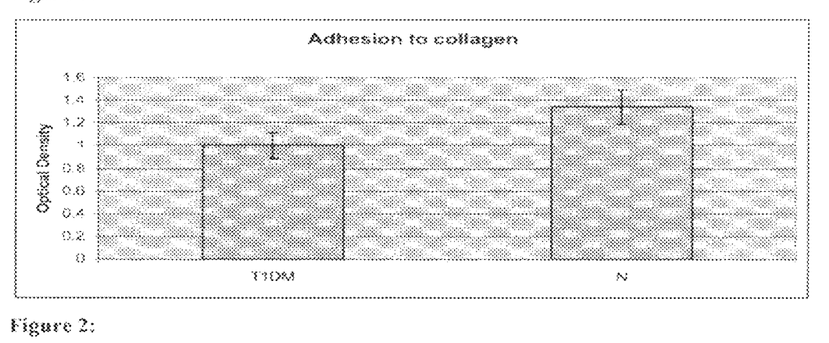
FIG. 2: Adhesion to collagen in T1DM and healthy volunteers
Figure 3:
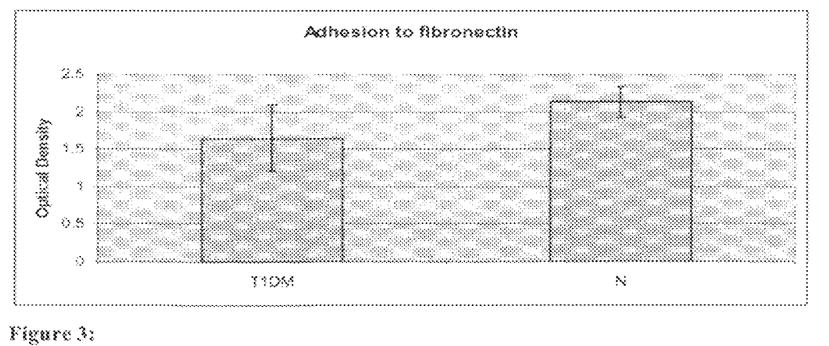
FIG. 3: EPC adhesion to fibronectin in T1DM and healthy volunteers.

Patients with T1DM have normal adhesion to collagen (1.00+/−0.11 vs 1.34+/−0.15, p=0.13) (FIG. 2) and fibronectin (1.65+/−0.44 vs 2.13+/−0.20, p=0.16) (FIG. 3).

Adhesion to Endothelial Cells

Figure 4:
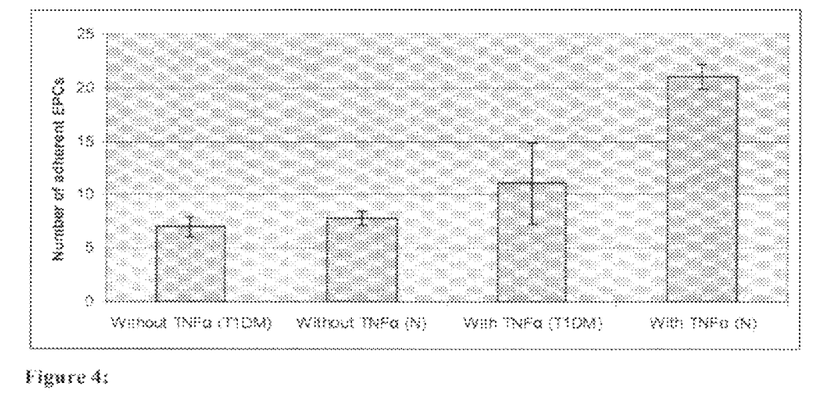
FIG. 4: EPC adhesion to human umbilical vein endothelial cells.

The effect of diabetes on EPC adhesion to endothelial cells was next assessed in quiescent endothelial cells and after exposure to TNF-α. EPCs derived from patients with poorly controlled T1DM demonstrated normal adhesion to quiescent endothelial cells (7.01+/−0.91 vs 7.79+/−0.68, p=0.54) but impaired adhesion to activated endothelial cells (11.05+/−0.01 vs 21.03+/−1.13, p=0.001) (FIG. 4).

Figure 5:
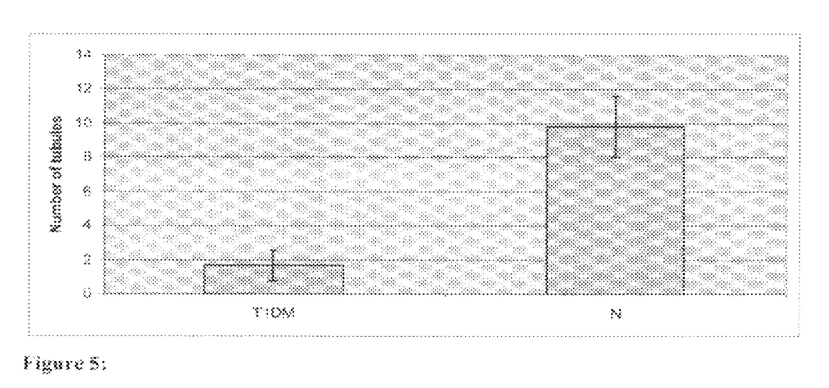
FIG. 5: The number of tubules formed by EPCs derived from patients with T1DM and healthy volunteers using Matrigel assay.
Figure 6:
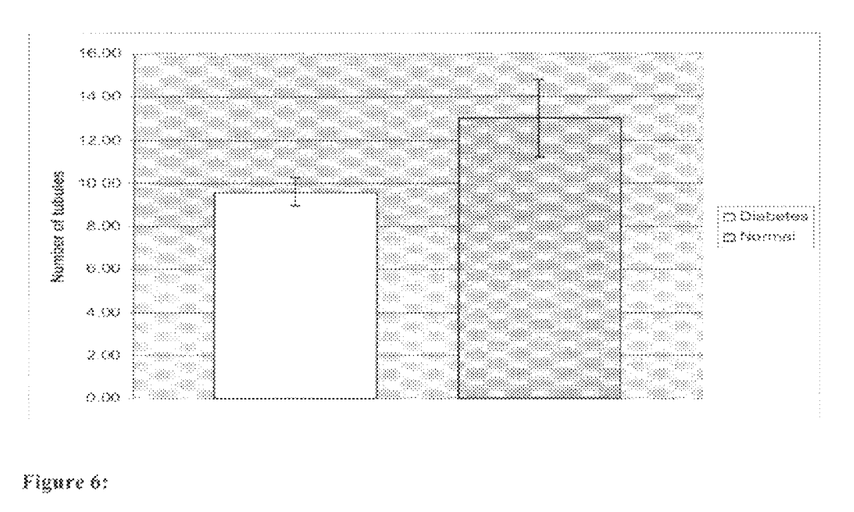
FIG. 6: The comparison between the number of tubules formed by EPCs derived from diabetic and non-diabetic rabbits using Matrigel assay. (9.6+/−1.77 vs 13.0+/−0.65: p=0.049).

Tubule Formation Using EPCs Derived from Patients with T1DM:

Formation of tubules in vitro a measure of the ability of EPC to participate in angiogenesis was next assessed. EPCs derived from patients with T1DM had impaired ability to form tubules compared to controls (1.7+/−0.9 vs 9.8+/−1.8, p=0.01) (FIG. 5). This defect was also seen in an animal model of insulin deficient diabetes mellitus when EPCs derived from alloxan-induced diabetic rabbits also showed an impaired ability to form tubules as compared to the EPCs derived from non-diabetic control rabbits (9.6+/−1.77 vs 13.0+/−0.65: p=0.049) (FIG. 6).

Expression of Osteopontin in EPCs from Patients with Poorly Controlled Diabetes Mellitus:

Using real time PCR, it was demonstrated that OPN expression is reduced in EPCs derived from patients with poorly controlled diabetes mellitus as compared to healthy volunteers.

Figure 7:
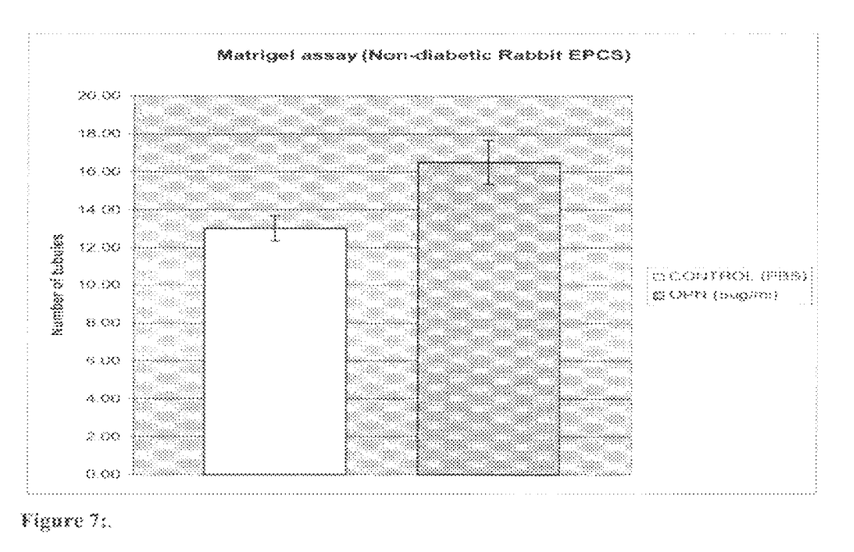
FIG. 7: The effect of OPN on the number of tubules formed by EPCs derived from non-diabetic rabbits using Matrigel assay. (13.0+/−0.65 vs 16.5+/−1.15: p=0.039; n=9).
Figure 8:
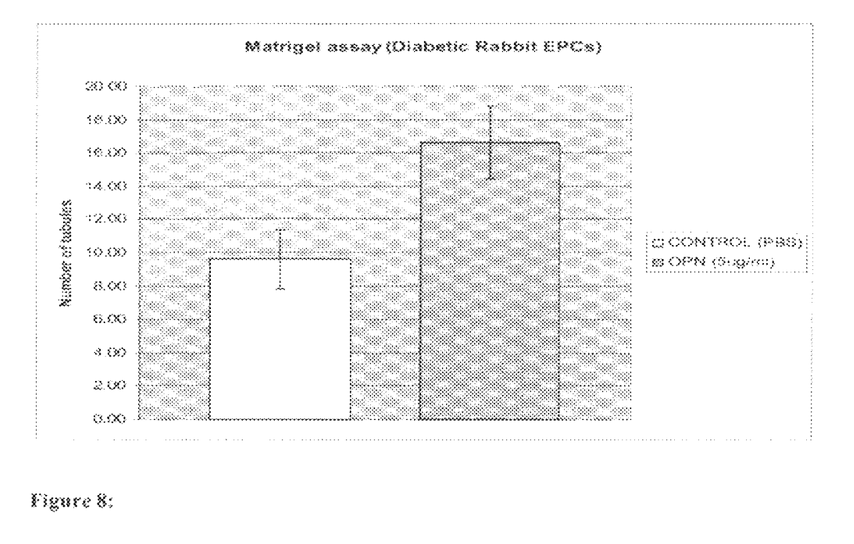
FIG. 8: The effect of OPN on the number of tubules formed by EPCs derived from diabetic rabbits using Matrigel assay. (9.6+/−1.77 vs 16.6+/−2.19: p=0.010; n=5).

Effect of OPN Supplementation on Tubule Formation:

Having demonstrated reduced expression of OPN in EPCs derived from patients with poorly controlled T1DM, it sought to determine whether exposure of EPCs to OPN could reverse this defect. To do this, the effect of OPN supplementation on EPC function in vitro was assessed. Incubation with OPN augmented the number of tubules formed by EPCs derived from non-diabetic rabbits (13.0+/−0.65 vs 16.5+/−1.15: p=0.039; FIG. 7). Incubation with OPN also augmented the number of tubules formed by EPCs derived from diabetic rabbits (9.88+/−2.48 vs 16.56+/−2.21; p=0.01) (FIG. 8).

The Effect of OPN on EPC Function is RGD-Dependent.

Figure 9:
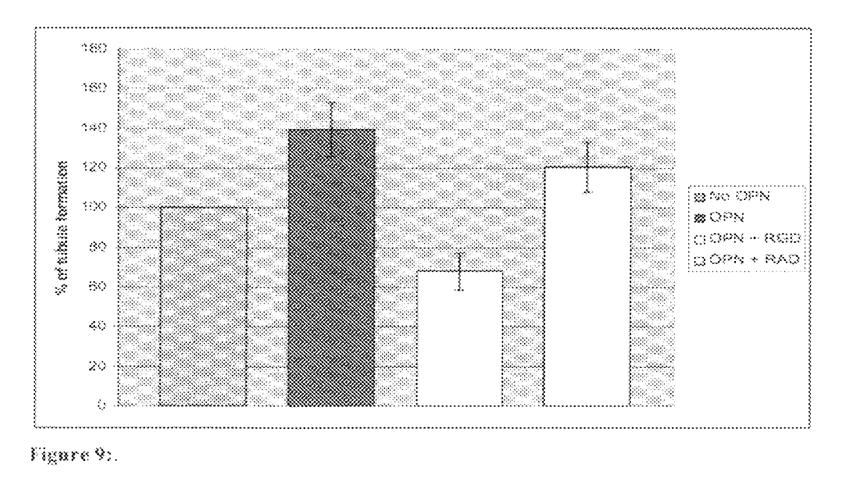
FIG. 9: The effect of OPN and RGD/RAD on the number of tubules formed by EPCs derived from diabetic rabbits using Matrigel assay.

Next, investigations were made to determine if the mechanism of OPN action is RGD-dependent. EPCs were co-incubated with OPN and RGD or RAD (Scrambled peptide). Co-incubation of EPCs with OPN and RGD, but not RAD, was associated with impaired EPC tubule formation. The results of this experiment show that the effect of OPN on EPC function is RGD-dependent (FIG. 9).

Microarray Analysis and Realtime PCR

Microarray analysis demonstrated that osteopontin was downregulated in the EPCs derived from the diabetic subjects. This was further validated using realtime PCR. The mean fold change were compared with the microarray results (Table 3).

Figure 10:
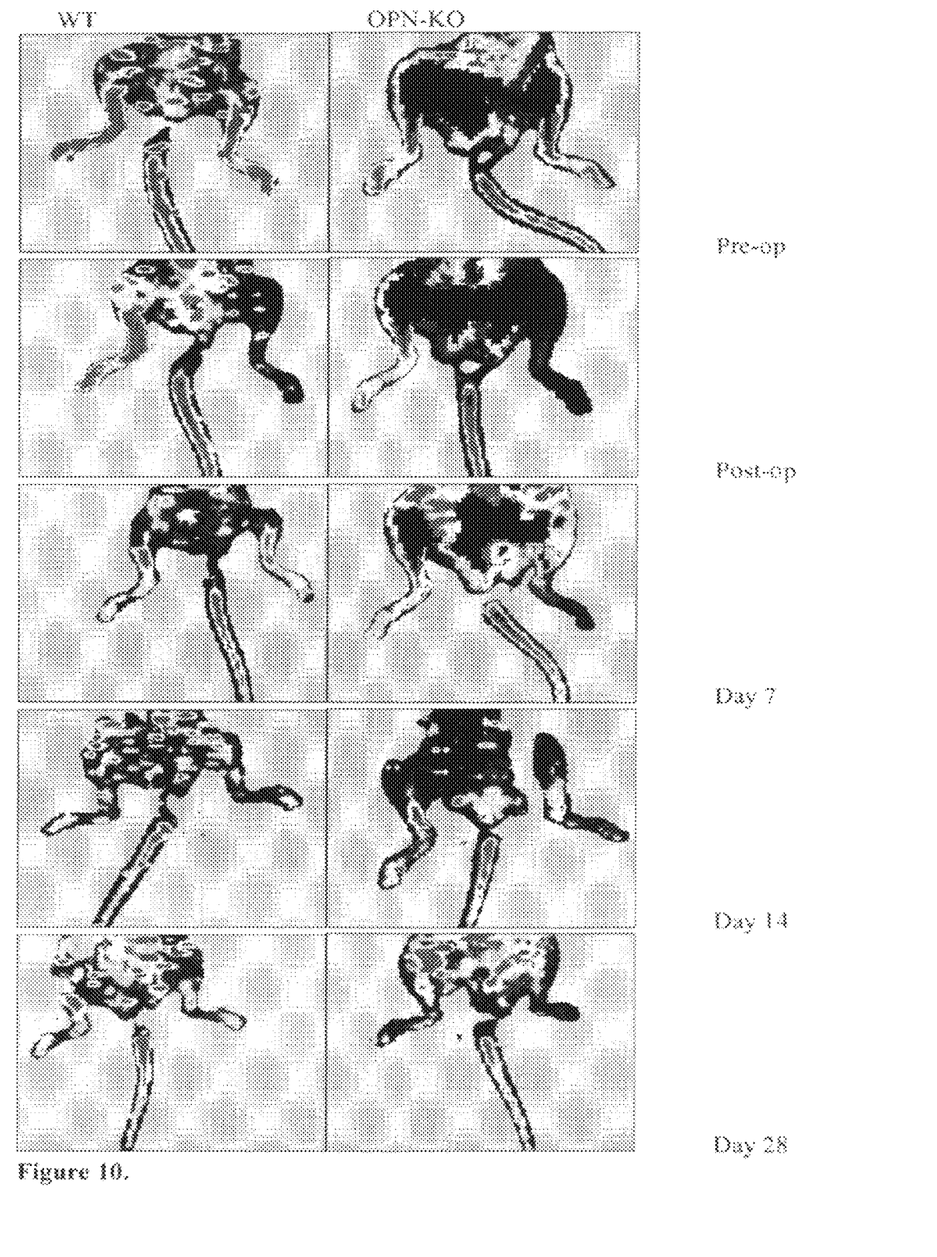
FIG. 10: Representative images of LDBF recorded at serial time points before and immediately, 7, 14 and 28 days after surgery in WT and OPN-KO mice.
Figure 11:
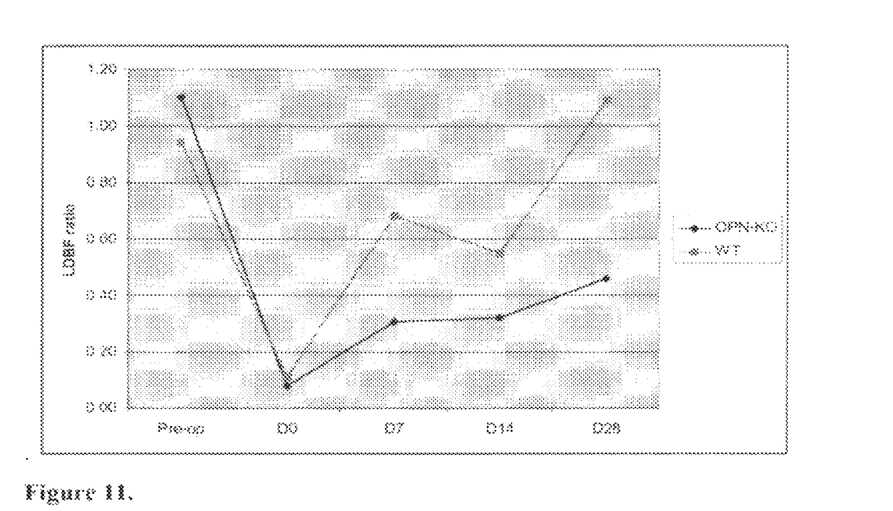
FIG. 11: Quantitative analysis of the ischemic/non-ischemic LDBF ratio in WT and OPN-KO mice (n=5 in each group).

Ischemia-Induced Angiogenesis in OPN-KO Mice:

To study the role of OPN in angiogenesis in vivo, the extent of angiogenesis in a murine model of unilateral hind limb ischemia was assessed. The blood flow was assessed in the WT and OPN-KO mice before and after the procedure. In OPN-KO mice, measurement of the LDBF ratio between the ischemic and the non-ischemic limb indicated that restoration of perfusion in the ischemic hind limb was significantly impaired. At day 7, 14 and 28 after surgery, LDPF ratio was reduced in the OPN-KO mice, 0.31±0.07 versus 0.68±0.11 (P=0.021), 0.32±0.03 versus 0.54±0.05 (p=0.006) and 0.45±0.06 versus 1.09±0.13 (P=0.002) for the WT mice respectively (FIGS. 10 and 11).

Figure 12:
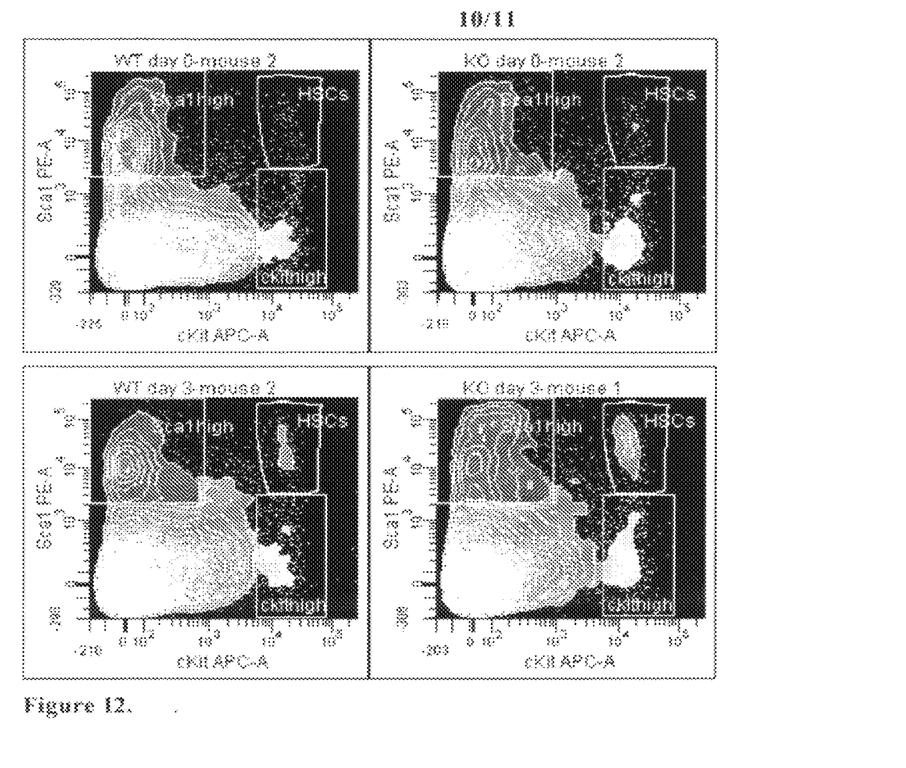
FIG. 12: Representative cytograms showing double staining with anti-Sca-1 and anti-c-kit antibodies for the determination of Sca-1+c-kit+ cells before and 3 days after induction of unilateral hind limb in WT and OPN-KO mice.
Figure 13:
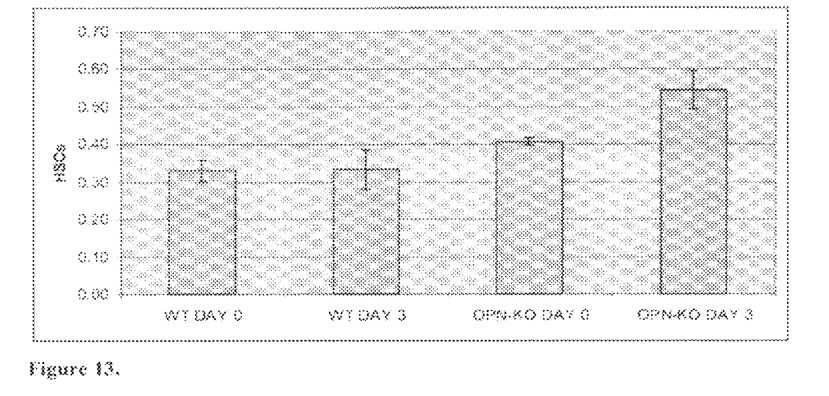
FIG. 13: EPC number in WT and OPN-KO mice before and 3 days after induction of unilateral hind limb ischemia.

Impairment of Angiogenesis is Not Due to Decreased EPC Recruitment:

Next, the role of EPC recruitment in the pathogenesis of the impaired angiogenesis observed in OPN knockout mouse was explored. For this, circulating EPC numbers were measured before and after induction of hind limb ischemia in OPN knockout and wild type animals. Flow cytometry analysis of EPC number was performed before and three days after the induction of hind limb ischemia. At day zero there were no differences in EPC number between both groups. Furthermore, EPC numbers increased in the OPN knockout mice 3 days after induction of hind limb ischemia (0.33±0.05 on day 0 versus 0.55±0.05 on day 3; p=0.036). This result suggests that OPN is not implicated in EPC mobilization. In contrast, EPC numbers did not increase 3 days after induction of hind limb ischemia in control mice (FIGS. 12 and 13).

A. Langendorff Treatment of Ex-Vivo Hearts

Osteopontin expression levels, as determined by realtime PCR, were decreased 5.14 fold in ischemic/reperfused rat heart in comparison with expression levels in the perfused sample.

Figure 14:
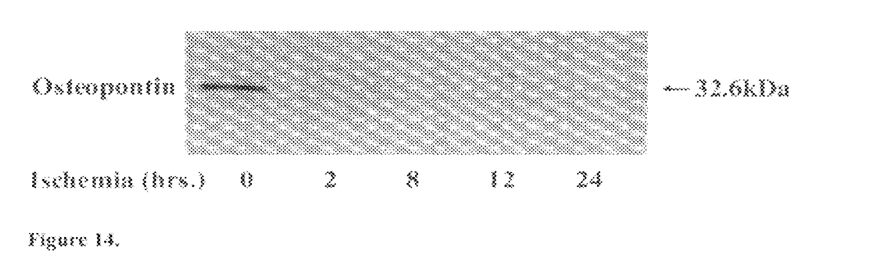
FIG. 14: Western blot analysis of OPN expression in primary neonatal rat cardiomyocytes in response to simulated ischemia.

B. Ischemia in Primary Neonatal Cardiomyocytes:

In rat neonatal cardiomyocytes primary cultures, subjected to conditions to simulate endogenous ischemia conditions, osteopontin protein expression levels were reduced, as determined by Western blot analysis (see FIG. 14.), in comparison to cardiomyocytes cultured under normal conditions. Osteopontin expression levels, measured on 2, 8, 12 and 24 hours, did not recover to pre-ischemia levels.

In summary, OPN mRNA and protein levels drop in response to ischemia or ischemia reperfusion.

Discussion

EPC number and function can be affected by various factors[15]. Reduced EPC number were demonstrated in patients with Type 1 and Type 2 DM[16,17]. However, microvascular complications were not excluded in these studies. It has recently been shown that diabetic retinopathy increases EPC number[20,21]. For this reason, a homogeneous population without diabetic retinopathy and other complications were chosen. It was desired to observe the effect of hyperglycaemia without other confounding factors in human with T1 DM.

The data showed that EPCs derived from patients with uncomplicated Type 1 Diabetes Mellitus have a reduced number. These cells showed normal adhesion to collagen and fibronectin. They also showed normal adhesion to quiescent endothelial cells but impaired adhesion to activated endothelial cells. EPCs derived from patients with T1DM have impaired ability to form tubules. These data were consistent with previous studies[16,17]. The role of OPN in EPC dysfunction in diabetes mellitus has been examined. It has been demonstrated for the first time that OPN expression was markedly reduced in EPCs isolated from subjects with poorly controlled T1DM. This result is the opposite of the effect observed by Loomans et al using microarray analysis[22]. The reason for the discrepancy is unclear but may be due the patient population studied. Furthermore, it has been demonstrated that EPC dysfunction was reversed when cells from diabetic animals were cultured in the presence of recombinant OPN. The effect of OPN on EPC function was also seen in cells from non-diabetic animals in which increased tubule formation was observed. Thus the invention could allow treatment of diseases with are associated with poor tubule formation, or problems with angiogenesis, which includes peripheral vascular disease, ulcer, ischaemic heart disease, and cerebrovascular disease, and subarachnoid haemmorrhage secondary to cerebral aneurysm and diabetic retinopathy. The effect of OPN on EPC function was reversed by RGD but not RAD showing the OPN effect is RGD-dependent.

The role of OPN in angiogenesis was next explored using an OPN knockout mouse. It was demonstrated that the restoration of perfusion in the ischemic hind limb was significantly impaired in OPN-KO mice. At day 7 after surgery, LDPF ratio in the OPN-KO mice was approximately half that of the WT mice. This impairment in blood flow recovery persisted up to 28 days after the surgery, suggesting that the absence of OPN impairs neovascularisation in the murine model of unilateral hind limb ischemia. This defect could be due to decreased mobilization or impairment of EPC incorporation into new vessels at the site of ischemia. The results show increased circulating levels of EPCs after hind limb ischemia in the OPN knockout suggests that impaired mobilization is not the mechanism. This hypothesis is supported by data from Ballard et al who have shown that the expression of OPN did not differ from baseline up to seven days after the induction of mid-dorsal cutaneous wound in diabetic mice. The OPN level subsequently increased at day 7 and remained constitutively higher for a further four days. The authors suggested that the low expression of OPN in diabetic mice may be in part responsible for the delayed healing of wounds in diabetic mice[33]. Therefore, reduced OPN expression in diabetic EPC may explain the propensity of diabetic subjects to macrovascular complications.

Osteopontin exists as a secreted cytokine or adhesion molecule constitutively expressed in healthy myocardium. Its expression is increased in non-myocytes following myocardial infarction to protect cellular viability and aid adaptive remodelling. Loss of osteopontin impairs compensatory fibrosis and hypertrophy leading to decreased cardiac performance. Osteopontin expression is also markedly increased in cardiomyocytes by myocardial infarction and heart failure. The mechanism of osteopontin cardioprotection is largely unknown. Osteopontin suppresses cytokine-induced nitric oxide synthase expression, preventing nitric oxide production and contractile impairment. Cellular signalling is mediated through cell surface integrin receptor binding. Integrin receptors communicate changes in the extracellular matrix to the cytoskeleton. Increased expression of osteopontin is accompanied by the increased expression of its cardiac-receptor β1 integrin during hypertrophy. Anti-integrin antibody blocked angiotensin II induced cardiac remodelling an effect also blocked by anti-osteopontin antibody, suggesting signalling of angiotensin II proceeds via osteopontin.

In osteopontin-deficient cardiac fibroblasts oxidative stress induced necrosis unlike wild type cells where apoptosis was predominant. This necrotic death was reduced on endogenous re-expression of osteopontin. However, in vivo study of myocardial infracted mouse hearts, have shown osteopontin deficient hearts to have the same number of apoptotic myocytes as wild type hearts.

Conclusion

EPC dysfunction in diabetes mellitus is associated with reduced OPN expression and can be reversed by OPN supplementation, which may explain why diabetic subjects are more prone to vascular complications. Furthermore the studies in the OPN knockout animals confirm the crucial role of OPN in angiogenesis. The results suggest that this effect may be related to lower OPN expression in EPCs. EPC dysfunction in diabetes mellitus is due to reduced OPN expression identifying a new therapeutic target for this disorder.

The words "comprises/comprising" and the words "having/including" when used herein with reference to the present invention are used to specify the presence of stated features, integers, steps or components but does not preclude the presence or addition of one or more other features, integers, steps, components or groups thereof.

It is appreciated that certain features of the invention, which are, for clarity, described in the context of separate embodiments, may also be provided in combination in a single embodiment. Conversely, various features of the invention which are, for brevity, described in the context of a single embodiment, may also be provided separately or in any suitable sub-combination.

References

1. Asahara T, Murohara T, Sullivan A, Silver M, van der Zee R, Li T, Witzenbichler B, Schatteman G, Isner J M. *Science*. 1997; 275:964-7.
2. Kalka C, Masuda H, Takahashi T, Kalka-Moll W M, Silver M, Kearney M, Li T, Isner J M, Asahara T. *Proc Natl Acad Sci USA*. 2000; 97:3422-7.
3. Kubota Y, Kishi K, Satoh H, Tanaka T, Nakajima H, Nakajima T. *Cell Transplant*. 2003; 12:647-57.
4. Griesc D P, Ehsan A, Melo L G, Kong D, Zhang L, Mann M J, Pratt R E, Mulligan R C, Dzau V J. *Circulation*. 2003; 108:2710-5.
5. He T, Smith L A, Harrington S, Nath K A, Caplice N M, Katusic Z S. *Stroke*. 2004; 35:2378-84.
6. Takahashi M, Nakamura T, Toba T, Kajiwara N, Kato H, Shimizu Y. *Tssue Eng*. 2004; 10:771-9.
7. Urbich C, Dimmeler S. *Trends Cardiovasc Med*. 2004; 14:318-22.
8. Gulati R, Jevremovic D, Peterson T E, Chatterjee S, Shah V, Vile R G, Simari R D. *Circ Res*. 2003; 93:1023-5.
9. Eggermann J, Kliche S, Jarmy G, Hoffmann K, Mayr-Beyrle U, Debatin K M, Waltenberger J, Beltinger C. *Cardiovasc Res*. 2003; 58:478-86.
10. Lin Y, Weisdorf D J, Solovey A, Hebbel R P. *Clin Invest*. 2000;105:71-7.
11. Hur J, Yoon C H, Kim H S, Choi J H, Kang H J, Hwang K K, Oh B H, Lee M M, Park Y B. *Arterioscler Thromb Vasc Biol*. 2004; 24:288-93.
12. Ingram D A, Mead L E, Tanaka H, Meade V, Fenoglio A, Mortell K, Pollok K, Ferkowicz M J, Gilley D, Yoder M C. *Blood*. 2004; 104:2752-60.
13. Walenta K, Friedrich E B, Sehnert F, Werner N, Nickenig G. *Biochem Biophys Res Commun*. 2005; 333:476-82.
14. Bellik L, Ledda F, Parenti A. *FEBS Lett*. 2005; 579:2731-6.
15. Liew A, Barry F, O'Brien T. *Bioessays*. 2006; 28:261-70.
16. Loomans C J, de Koning E J, Staal F J, Rookmaaker M B, Verseyden C, de Boer H C, Verhaar M C, Braam B, Rabelink T J, van Zonneveld A J. *Diabetes*. 2004; 53:195-9.
17. Tepper O M, Galiano R D, Capla J M, Kalka C, Gagne P J, Jacobowitz G R, Levine J P, Gurtner G C. *Circulation*. 2002; 106:2781-6.
18. Fadini G P, Miorin M, Facco M, Bonamico S, Baesso I, Grego F, Menegolo M, de Kreutzenberg S V, Tiengo A, Agostini C, Avogaro A. *J Am Coll Cardiol*. 2005; 45:1449-57.
19. Willing M, Sowers M, Aron D, Clark M K, Burns T, Bunten C, Crutchfield M, D'Agostino D, Jannausch M. *J Bone Miner Res*. 1998; 13:695-705.
20. Asnaghi V, Lattanzio R, Mazzolari G, Pastore M R, Ramoni A, Maestroni A, Ruggieri D, Luzi L, Brancato R, Zerbini G. *Diabetologia*. 2006.
21. Fadini G P, Sartore S, Baesso I, Lenzi M, Agostini C, Tiengo A, Avogaro A. *Diabetes Care*. 2006; 29:714-6.
22. Loomans C J, De Koning E J, Staal F J, Rabelink T J, Zonneveld A J. *Antioxid Redox Signal*. 2005; 7:1468-75.
23. Denhardt D T, Lopez C A, Rollo E E, Hwang S M, An X R, Walther S E. *Ann N Y Acad Sci*. 1995; 760:127-42.
24. Haubner R, Weber W A, Beer A J, Vabuliene E, Reim D, Sarbia M, Becker K F, Goebel M, Hein R, Wester H J, Kessler H, Schwaiger M. *PLoS Med*. 2005; 2:e70.
25. Uede T, Katagiri Y, Iizuka J, Murakami M. *Microbiol Immunol*. 1997; 41:641-8.
26. Hirama M, Takahashi F, Takahashi K, Akutagawa S, Shimizu K, Soma S, Shimanuki Y, Nishio K, Fukuchi Y. *Cancer Lett*. 2003; 198:107-17.

27. Zhou Y, Dai D L, Martinka M, Su M, Zhang Y, Campos E I, Dorocicz I, Tang L, Huntsman D, Nelson C, Ho V, Li G. *J Invest Dermatol.* 2005; 124:1044-52.
28. Hu Z, Lin D, Yuan J, Xiao T, Zhang H, Sun W, Han N, Ma Y, Di X, Gao M, Ma J, Zhang J, Cheng S, Gao Y. *Clin Cancer Res.* 2005; 11:4646-52.
29. Ito T, Hashimoto Y, Tanaka E, Kan T, Tsunoda S, Sato F, Higashiyama M, Okumura T, Shimada Y. *Clin Cancer Res.* 2006; 12:1308-16.
30. Wai P Y, Mi Z, Guo H, Sarraf-Yazdi S, Gao C, Wei J, Marroquin C E, Clary B, Kuo P C. *Carcinogenesis.* 2005; 26:741-51.
31. Muramatsu T, Shima K, Ohta K, Kizaki H, Ro Y, Kohno Y, Abiko Y, Shimono M. *Cancer Lett.* 2005; 217:87-95.
32. Rivard A, Silver M, Chen D, Kearney M, Magner M, Annex B, Peters K, Isner J M. *Am J Pathol.* 1999; 154: 355-63
33. Ballard V L, Sharma A, Duignan I, Holm J M, Chin A, Choi R, Hajjar K A, Wong S C, Edelberg J M. *Faseb J.* 2006; 20:717-9 ( ).
34. Tsuchida et al. *Circulation Research* 1994.
35. Gottlieb R A, The Journal of Clinical Investigation 1994, Fliss H, Circulation Research 1996

TABLE 1

Primer sequences for Real-Time PCR.

| Gene | Length | Start | Sequence (5'-3') |
|------|--------|-------|------------------|
| OPN  | 114    | 12    | CAGAGCACAGCATCGTCGG |
|      |        | 125   | GGCAAAAGCAAATCACTGCAA |

TABLE 1-continued

Primer sequences for Real-Time PCR.

| Gene | Length | Start | Sequence (5'-3') |
|------|--------|-------|------------------|
| Cyclophilin A | 103 | 378 | TGCTGGACCCAACACAAATG |
|      |        | 480   | CATGCCTTCTTTCACTTTGCC |

TABLE 2

Subjects' characteristics.

|  | T1DM | Healthy volunteers | P-value |
|---|------|--------------------|---------|
| Age (years) | 22.3 +/- 4.3 | 22.8 +/- 2.1 | NS |
| Gender | 3F:1M | 3F:1M | NS |
| HbA1c (%) | 12.5 +/- 1.5 | NA | |
| Duration of DM (Years) | 7 +/- 2.3 | NA | |

TABLE 3

Comparison of the osteopontin gene expression (fold changes) between microarray and realtime PCR results.

| Gene | Gene code | Microarray | Realtime PCR |
|------|-----------|------------|--------------|
| OPN  | M83248    | -9.6       | -28.54       |

TABLE 4

Oligonucleotide Primers

| Gene | Forward 5'-3' | Reverse 5'-3' | Product Size bp |
|------|---------------|---------------|-----------------|
| Osteopontin | CGATGGAGACCATGCAGAGA | GCTTGTGTGCTGGCAGTGA | 105 |
| GAPDH | CCAGCAAGGATACTGAGAGCAA | GGATGGAATTGTGAGGGAGATG | 101 |

TABLE 5

Altered gene expression in response to I/R when compared to perfused hearts

| Gene | Q PCR | Comparison |
|------|-------|------------|
| Osteopontin | -5.14 | I/R vs Perfused |

The invention claimed is:

1. A pharmaceutical composition comprising an exogenous osteopontin protein and osteoipontin-activated endothelial progenitor cells or mesenchymal stem cells, wherein the endothelial progenitor cells or mesenchymal stem cells have been activated by incubating the cells with osteopontin protein.

2. The pharmaceutical composition of claim 1, wherein the activated endothelial progenitor cell or activated mesenchymal stem cell expresses osteopontin.

3. The pharmaceutical composition of claim 2, wherein the activated endothelial progenitor cell or activated mesenchymal stem cell is genetically modified to augment osteopontin gene expression.

* * * * *

SEQUENCE LISTING

<160> NUMBER OF SEQ ID NOS: 8

<210> SEQ ID NO 1
<211> LENGTH: 19
<212> TYPE: DNA
<213> ORGANISM: Artificial Sequence
<220> FEATURE:
<223> OTHER INFORMATION: OPN forward primer

<400> SEQUENCE: 1

-continued

| cagagcacag catcgtcgg | 19 |

<210> SEQ ID NO 2
<211> LENGTH: 21
<212> TYPE: DNA
<213> ORGANISM: Artificial Sequence
<220> FEATURE:
<223> OTHER INFORMATION: OPN reverse primer

<400> SEQUENCE: 2

| ggcaaaagca aatcactgca a | 21 |

<210> SEQ ID NO 3
<211> LENGTH: 20
<212> TYPE: DNA
<213> ORGANISM: Artificial Sequence
<220> FEATURE:
<223> OTHER INFORMATION: Cyclophilin A forward primer

<400> SEQUENCE: 3

| tgctggaccc aacacaaatg | 20 |

<210> SEQ ID NO 4
<211> LENGTH: 21
<212> TYPE: DNA
<213> ORGANISM: Artificial Sequence
<220> FEATURE:
<223> OTHER INFORMATION: Cyclophilin A reverse primer

<400> SEQUENCE: 4

| catgccttct ttcactttgc c | 21 |

<210> SEQ ID NO 5
<211> LENGTH: 20
<212> TYPE: DNA
<213> ORGANISM: Artificial Sequence
<220> FEATURE:
<223> OTHER INFORMATION: Osteopontin forward primer

<400> SEQUENCE: 5

| cgatggagac catgcagaga | 20 |

<210> SEQ ID NO 6
<211> LENGTH: 19
<212> TYPE: DNA
<213> ORGANISM: Artificial Sequence
<220> FEATURE:
<223> OTHER INFORMATION: Osteopontin reverse primer

<400> SEQUENCE: 6

| gcttgtgtgc tggcagtga | 19 |

<210> SEQ ID NO 7
<211> LENGTH: 22
<212> TYPE: DNA
<213> ORGANISM: Artificial Sequence
<220> FEATURE:
<223> OTHER INFORMATION: GAPDH forward primer

<400> SEQUENCE: 7

| ccagcaagga tactgagagc aa | 22 |

<210> SEQ ID NO 8
<211> LENGTH: 22
<212> TYPE: DNA
<213> ORGANISM: Artificial Sequence
<220> FEATURE:

```
<223> OTHER INFORMATION: GAPDH reverse primer

<400> SEQUENCE: 8
ggatggaatt gtgagggaga tg                                              22
```